United States Patent
Kotowski et al.

(10) Patent No.: US 9,500,621 B2
(45) Date of Patent: Nov. 22, 2016

(54) LEAKAGE CURRENT SENSE CIRCUIT FOR ERROR DETECTION IN AN IMPROVED CAPILLARY ELECTROPHORESIS-ELECTROSPRAY IONIZATION-MASS SPECTROMETRY SYSTEM

(71) Applicant: Beckman Coulter, Inc., Brea, CA (US)

(72) Inventors: Peter S. Kotowski, Yorba Linda, CA (US); Sunil S. Deliwala, Placentia, CA (US); Stephen A. Frye, Chino, CA (US)

(73) Assignee: Beckman Coulter, Inc., Brea, CA (US)

( * ) Notice: Subject to any disclaimer, the term of this patent is extended or adjusted under 35 U.S.C. 154(b) by 771 days.

(21) Appl. No.: 13/908,861

(22) Filed: Jun. 3, 2013

(65) Prior Publication Data

US 2013/0319862 A1 Dec. 5, 2013

Related U.S. Application Data

(60) Provisional application No. 61/655,433, filed on Jun. 4, 2012.

(51) Int. Cl.
*G01N 27/447* (2006.01)
*G01R 31/02* (2006.01)
(Continued)

(52) U.S. Cl.
CPC .. *G01N 27/44704* (2013.01); *G01N 27/44713* (2013.01); *H01J 49/022* (2013.01); *H01J 49/165* (2013.01); *G01R 31/025* (2013.01)

(58) Field of Classification Search
CPC .................. G01N 27/44704; G01N 27/44713; G01R 31/25; H01J 49/022; H01J 49/165
(Continued)

(56) References Cited

U.S. PATENT DOCUMENTS 4,716,487 A * 12/1987 Horvath ............... H02H 3/17
318/490
2004/0018638 A1 1/2004 Shoji et al.
(Continued)

FOREIGN PATENT DOCUMENTS

CN 102016559 A 4/2011
WO 2009/011488 A1 1/2009

OTHER PUBLICATIONS

Beckman Coulter, Inc.; "CESI8000 High Performance Separation: ESI Module,"; located at https://www.beckmancoulter.com/wsrportal/bibliography?docname=CESI+8000+Spectrometer+Brochure.pdf; Feb. 1, 2014; 8 pages.
(Continued)

*Primary Examiner* — Thienvu Tran
*Assistant Examiner* — Kevin J Comber
(74) *Attorney, Agent, or Firm* — Kilpatrick Townsend & Stockton LLP

(57) ABSTRACT

Aspects of the present innovations relate to improved systems that may perform capillary electrophoresis (CE) and CE in conjunction with electrospray ionization (ESI) as an input to a mass spectrometry system (MS). Embodiments may use a current sense circuit at a high voltage output from an MS-ESI power supply in conjunction with additional elements to identify fault conditions associated with leakage current, to confirm the continuity of CE connections, and to provide improved system protection.

24 Claims, 6 Drawing Sheets

(51) Int. Cl.
H01J 49/02 (2006.01)
H01J 49/16 (2006.01)

(58) Field of Classification Search
USPC .................................................. 361/42
See application file for complete search history.

(56) References Cited

U.S. PATENT DOCUMENTS

2005/0072934 A1* 4/2005 Frazer .................. H01J 49/165
250/424
2006/0027744 A1 2/2006 Stults et al.
2010/0001181 A1 1/2010 Moini

OTHER PUBLICATIONS

Beckman Coulter, Inc.; "Extending the Reach of Mass Spectrometry. CESI 8000 High Performance Separation—ESI Module with OptiMS Technology,"; BR-15151A; located at http://www.lapplan.ie/admin/docuemtns/CESI_800.pdfl Jun. 2, 2011; 12 pages.
Busnel, Jean-Marc et al.; "High Capacity Capillary Electrophoresis-Electrospray Ionization Mass Spectrometry: Coupling a Porous Sheathless Interface with Transient-Isotachophoresis,"; *Anal. Chem.*; 2010; vol. 82; pp. 9476-9483.
Haselberg; Rob et al.; "Performance of a Sheathless Porous Tip Sprayer for Capillary Electrophoresis-Electrospray Ionization-mass Spectrometry of Intact Proteins,"; *Journal of Chromatography A*; 2010; vol. 1217; pp. 7605-7611.
International Search Report and Written Opinion mailed on Jul. 11, 2014 for PCT Patent Application No. PCT/US2013/044093, 18 pages.
Moini, M.; "Simplifying CE-MS Operation. 2. Interfacing Low-Flow Separation Techniques to Mass Spectrometry Using a Porous Tip,"; *Anal. Chem.* 2007; vol. 79; pp. 4241-4246.
Thomas Net News; "Floating Power Supply Suits Mass Spectrometry Applications,"; Aug. 18, 2008; locate at http://news.thomasnet.com/fullstory/Floating-Power-Supply-Suits-Mass-Spectromety-Applications-547855; 4 pages.
Thorn, J.; "New OptiMS Technology: Extending the Reach of Mass Spectrometry by High Efficiency CESI-MS,"; *Beckman Coulter, Inc.*; located at http://www.per-form.hu/dokumentacio/tomeg/Jim_Thorn_CESI_MS_AB_SCIEX.pdf; Jan. 1, 2011; 23 pages.
Chinese Office Action mailed on Mar. 10, 2016 for CN Patent Application No. 201380028845.5, with English Translations, 10 pages.

* cited by examiner

LEAKAGE CURRENT SENSE CIRCUIT FOR ERROR DETECTION IN AN IMPROVED CAPILLARY ELECTROPHORESIS-ELECTROSPRAY IONIZATION-MASS SPECTROMETRY SYSTEM

CROSS-REFERENCES TO RELATED APPLICATIONS

This application claims priority to U.S. Provisional Patent Application No. 61/655,433, filed Jun. 4, 2012, entitled "LEAKAGE CURRENT SENSE CIRCUIT FOR ERROR DETECTION IN AN IMPROVED CAPILLARY ELECTROPHORESIS-ELECTROSPRAY IONIZATION-MASS SPECTROMETRY SYSTEM," which is herein incorporated by reference in its entirety for all purposes.

BACKGROUND

This invention relates to electrophoresis and to capillary electrophoresis used in conjunction with electrospray ionization mass spectrometry.

Electrophoresis is fundamentally the movement of charged particles within an applied electric field. Capillary electrophoresis (CE) is a known process. In capillary electrophoresis, a sample is injected at one end of the capillary. A detector is attached on the capillary at the other end of the capillary distant from the sample. A voltage is applied along the length of the capillary.

With the electric potential applied, two separate flow effects occur. The first of these flow effects is a gross sample flow effect. The sample moves as a mass into the capillary. The second of these flow effects is the electrophoretic flow. This causes the constituents of the sample having differing electric charges to move relative to the main stream of fluid within the capillary. The portions of the sample having differing electric charges are thereby separated in the capillary.

Different detectors may be used to analyze the sample after the separation has occurred. In a system that combines capillary electrophoresis with electrospray ionization (ESI) and mass spectrometry (MS), the output of the capillary is input to an electrospray assembly. The electrospray ionization is accomplished by placing a high voltage potential at the outlet of the separation capillary with respect to the capillary inlet to the mass spectrometer. The separation capillary also requires a high voltage potential placed between its inlet and outlet. The separated portions of the sample are dispersed by the electrospray into a fine aerosol as they exit the capillary. The droplets of the aerosol are then observed by mass spectrometry.

Capillary electrophoresis coupled with electrospray ionization and mass spectrometry is a relatively difficult procedure. The capillary must be mechanically connected to the rest of the system and positioned with respect to a detector. The capillaries are small and fragile, and the alignment process with the electrospray ionization assembly into the mass spectrometer may be difficult, time consuming, and may damage the capillary.

The system is further complicated by a variety of factors, such as the need to cool the capillary. This cooling is required because the small capillary is subject to electrical resistance heating during the period of time electrophoresis potential voltage is applied. A small current under high voltage flowing in the capillary generates heat. The cooling is required to prevent damage to the capillary and to prevent variations in temperature during analysis of the sample from impacting the results of the analysis. Excess heat may cause diffusion of the separated portions of the sample that migrate through the capillary at different speeds. The heat and its resultant diffusion degrade separation and following classification result that is the purpose of using electrophoresis.

An additional complication is that capillary electrophoresis systems and ESI-MS systems are structured as two separate systems that must be configured together to perform a CE ESI-MS measurement. Different interfaces and standard connections between different types and brands of instruments cause interconnection issues that also may create a safety hazard for users if the connections are not set properly, especially given the high voltages involved in both systems.

There is therefore a need for improved CE ESI-MS systems that improve functionality and interconnection systems between CE and ESI-MS systems. There is a need for a CE system comprising an error detection circuit suitable for individually interfacing with two or more types of electrospray ionization-mass spectrometers.

SUMMARY

The present invention relates to an improved system where capillary electrophoresis is used in conjunction with electrospray ionization mass spectrometry. In particular, various embodiments include a current sense circuit to enable error detection for CE ESI-MS systems.

In one potential embodiment, a capillary electrophoresis (CE) system for use in conjunction with electrospray ionization mass spectrometry (ESI-MS) systems includes a capillary electrophoresis high voltage power supply (CE HV supply) having an output and a return; a mass spectrometer electrospray ionization high voltage power supply (MS HV supply) having an output and a return; and a current sense circuit having an input and an output where the input of the current sense circuit is coupled to the output of the MS HV supply, such that the MS HV supply is coupled to the spray end of a separation capillary via the current sense circuit. In some embodiments, such systems include a current sense circuit comprising a sense resistor coupled to an absolute value amplifier and a direct current to direct current (DC/DC) converter coupled to the absolute value amplifier; the DC/DC converter powers and isolates the current sense circuit so that the current measurement and absolute value circuits are floating on the MS HV supply. In some embodiments the DC/DC converter comprises a circuit built in for transmitting the current sense signals from the floating to the grounded side of the circuit, whereas in other embodiments a separate circuit is used to transmit the signals.

Some such floating embodiments include a voltage protection device such as an at least one gas discharge tube, or other similar device, which couples the ground of the current sense circuit, which is floating on the ESI high voltage power supply (MS HV supply), to a system ground, such as a system chassis ground, without affecting the function of the circuit.

Additional alternative embodiments include systems that measure delivered and return current at a CE HV power supply and include information related to measurement errors and offsets. In some embodiments such information is used with the sense circuit information to identify a leakage current by subtracting return, sense, and offset currents from CE HV supply delivered current. In some embodiments the system signals an error if the leakage current exceeds a predetermined threshold. Additionally or alternatively, in some embodiments the system initiates an automatic shutdown when a number of leakage current readings reaches or exceeds the predetermined threshold.

Some additional alternative embodiments include a capillary electrophoresis electrospray ionization mass spectrometry (CE-ESI-MS) system comprising: a mass spectrometry (MS) high voltage power supply having a first output, a first return and a first ground; a capillary electrophoresis (CE) high voltage power supply having a second output, a second return and a second ground, said second ground including a connection to the first ground of the MS HV power supply; a MS electrical path connected to a ground that provides the mass spectrometry HV power supply first return from the first output to the first ground via a mass spectrometry load; a CE electrical path that provides the CE HV power supply second return from the second output to the second ground via a separation capillary, wherein a resistive electrical path of the separation capillary is connected to the first output of the MS HV power supply and wherein the first output is electrically coupled to the second return via the separation capillary; and a current sense circuit coupled to the mass spectrometry power supply output and the separation capillary via a capillary junction.

Some additional alternative embodiments include a capillary electrophoresis system with a means for individually coupling the CE high voltage power supply to a plurality of different mass spectrometers of both hot needle and grounded needle type, and a means for sensing a current at the output of a mass spectrometer high voltage power supply connection to the CE system. Non-limiting examples of hot needle types of mass spectrometers include a Thermo mass spectrometer, an AB-Sciex mass spectrometer, and a Waters mass spectrometer. A non-limiting example of a grounded needle type of mass spectrometer is a Bruker mass spectrometer.

Some embodiments additionally include methods such as measuring a current from an electrospray terminal to a mass spectrometry MS DC high voltage (HV) power supply at an output of the mass spectrometry (MS) DC power supply and creating a fault error when a calculated leakage current exceeds a threshold. Some embodiments also include methods such as measuring a delivered current at an output of a capillary electrophoresis (CE) power supply, measuring a return current at the return of the CE power supply, identifying an offset current associated with system inaccuracy, and measuring a sense current at a current sense circuit at the output of a MS HV power supply, as well as identifying a leakage current by subtracting the return current, the sense current, and the offset current from the delivered current.

Further alternative embodiments include systems, non-transitory computer readable storage media, computer memory, or a combination thereof, in conjunction with processors that function with computer readable instructions that, when executed, perform methods of measuring a CE leakage current at an output of the mass spectrometry (MS) HV power supply and create a fault error when the leakage current exceeds a threshold.

DETAILED DESCRIPTION OF THE INVENTION

The present invention relates to improved systems and methods integrating capillary electrophoresis (CE) with mass spectrometry (MS). In some embodiments such a system provides an integrated structure that as a whole is used to separate samples containing molecules such as protein complexes, proteins, peptides, glycans or drugs/metabolites using CE, and characterize/identify the separated molecules using MS. The innovations herein in certain embodiments apply to any capillary electrophoresis (CE) system coupled to a mass spectrometer (MS) system via electrospray ionization (ESI) and, in other embodiments, are structured as an improved CE system that has an interface to be used with a plurality of MS systems.

In particular, certain embodiments show improved systems including a current sense circuit that interfaces with a high voltage output of a MS ESI power supply to provide fault detection in a manner not previously known.

A CE ESI-MS configuration circuit consists of two main parts: a CE portion and an MS portion. While each part of the circuit performs a different function, with the CE portion performing separation and the ESI-MS performing further electrospray functionality, the two parts are not electrically exclusive. The CE power supply delivers voltage across the separation capillary, with the MS power supply providing the return path. Any leakage current, due to, as a non-limiting example, salt build-up around the electrode, cannot be detected by standard current detection systems within the CE power supply. This is because in the coupled electrical structure, the current leaving the CE supply bypasses the High Voltage Return Input (124, 224) and returns to the CE supply through the System Ground (170, 270) via the MS ESI power supply. The delivered and return currents are the same because the current returning to the CE power supply includes both the current across the electrode and the leakage current from the salt build-up which is the sum of all current delivered by the CE high voltage power supply. This is explained in further detail below.

In certain embodiments, therefore, a current sense circuit coupled to the high voltage output of the mass spectrometer power supply allows for comparing the delivered current to the current flowing through the proper return path, that being the MS ESI high voltage power supply, while excluding any leakage current caused by, as non-limiting examples, salt build-up or arcing. If there is a difference between the delivered current and the current sensed at the high side of the MS ESI power supply, in some embodiments this is read by a controller or computing device as meaning that more current is being delivered to some leakage path, and the system can flag an error.

Figure 1A:
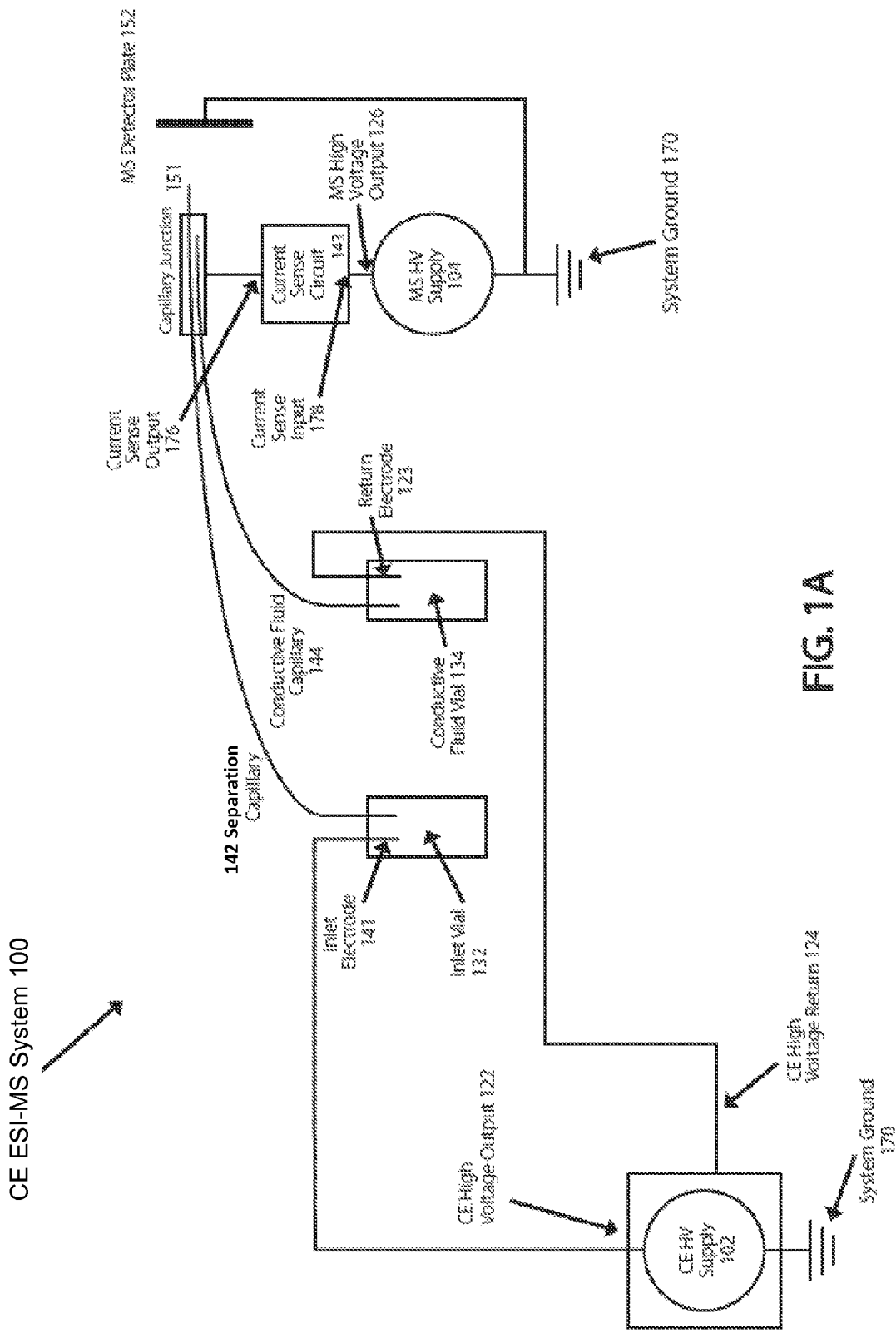
FIG. 1A illustrates an electrical diagram of one potential implementation of a CE-ESI mass spectrometry system in accordance with one potential embodiment of the innovations presented herein.
Figure 1B:
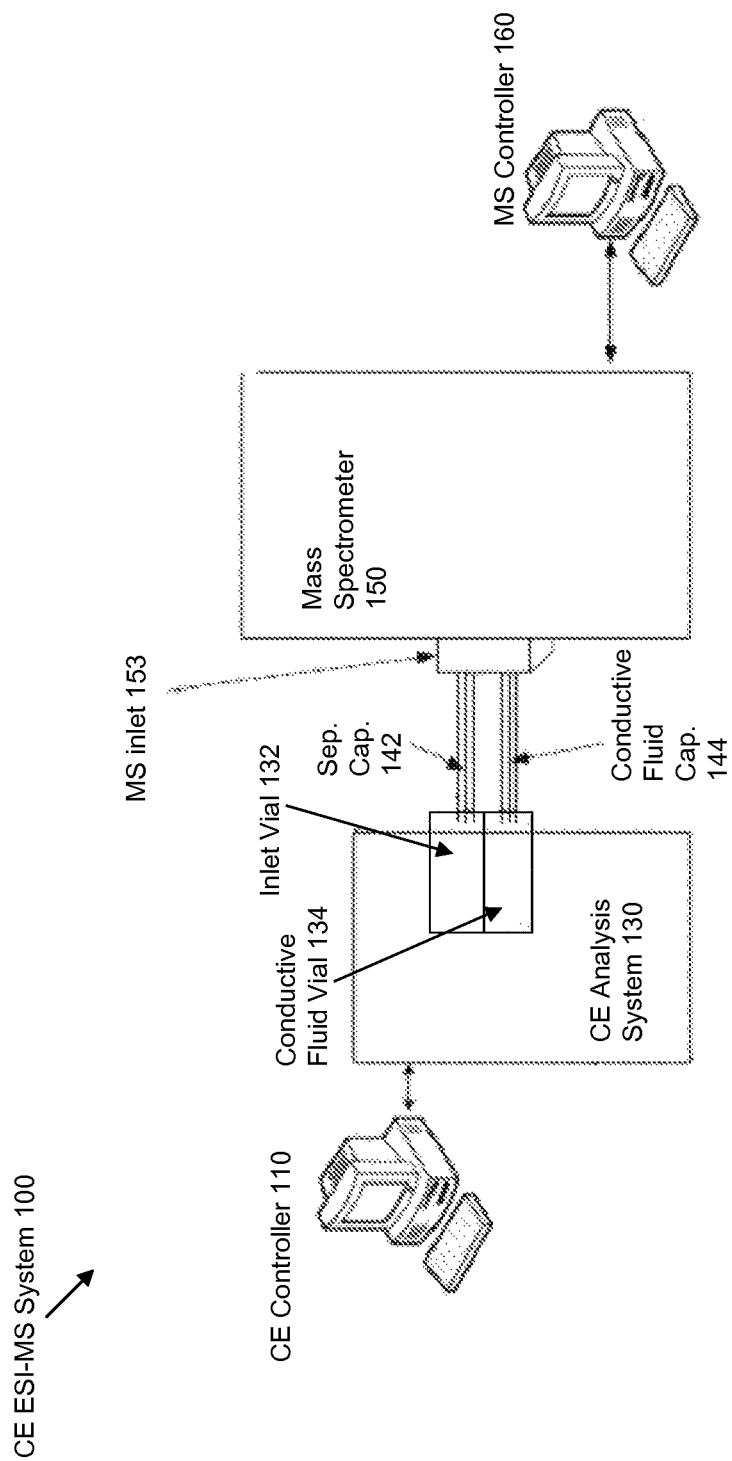
FIG. 1B illustrates a diagram of one potential implementation of a CE-ESI mass spectrometry system in accordance with one potential embodiment of the innovations presented herein.
Figure 1C:
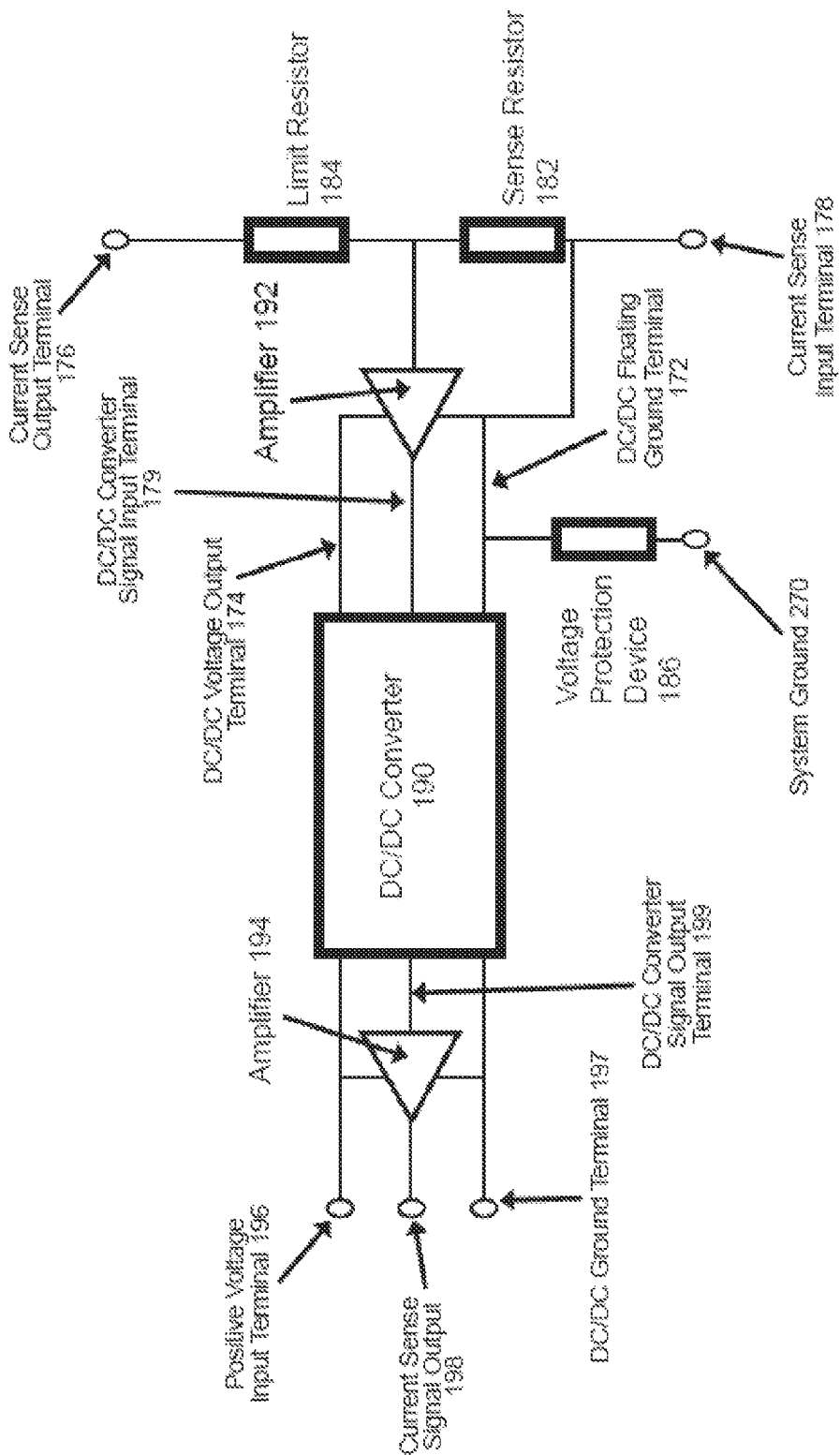
FIG. 1C illustrates one potential implementation of a leakage detection sense circuit for use in conjunction with one potential implementation of a CE-ESI mass spectrometry system.

FIGS. 1A, 1B, and 1C show various aspects of one potential implementation of a system according to the present innovations. FIG. 1A shows an electrical diagram of CE ESI-MS System 100 which includes capillary electrophoresis high voltage supply (CE HV supply) 102 and mass spectrometer ESI high voltage supply (MS HV supply) 104, inlet electrode 141, inlet vial 132, separation (or sample) capillary 142, capillary junction 151, conductive fluid capillary 144, conductive fluid vial 134, return electrode 123, mass spectrometer detector plate 152, and current sense circuit 143. The CE HV supply 102 and the MS HV supply 104 are electrically coupled such that the MS high voltage output 126 is coupled to the Capillary Junction 151, via the Current Sense Circuit 143. A first voltage from CE HV supply 102 is therefore placed across separation capillary 142 from CE high voltage output 122 to capillary junction 151, and a second voltage from MS HV supply (104) is placed across the gap from capillary junction 151 to MS detector plate 152.

FIG. 1B shows a system level block diagram of CE ESI-MS system 100. This system shows inlet vial 132, conductive fluid vial 134, separation capillary 142 (which is also be referred to as the sample capillary), and conductive fluid capillary 144, just as in FIG. 1A. FIG. 1B further shows CE analysis system 130, mass spectrometer 150, CE controller 110, and MS controller 160. In some embodiments, CE analysis system 130 includes or is coupled to CE HV supply 102; similarly, in some embodiments, mass spectrometer 150 includes or is coupled to MS HV supply 104. In various alternative embodiments, current sense circuit 143 is included in either CE analysis system 130, mass spectrometer 150, MS inlet 153, or as a separate box or component coupled to any of the elements of FIG. 1A or 1B.

The basic functionality of the system is for a sample to be selected and placed in inlet vial 132. CE HV power supply 102 provides a high voltage which in some embodiments, as a non-limiting example, is on the order of 30 kV, across separation capillary 142. Conductive fluid capillary 144 introduces a conductive fluid at capillary junction 151 which is inside a sprayer housing attached to a mass spectrometer inlet 153 to enable electrospray ionization of the material separated in the separation capillary. In some embodiments mass spectrometer 150 then analyzes the separated sample using the voltage from MS ESI HV supply 104.

For a CE analysis system 130 operating in stand alone mode, the CE HV supply 102 can detect a current leak by comparing the current delivered to the separation capillary 142 at the inlet electrode 141 to the current returning through the return electrode 123. If there is leakage, the leakage current will make its way back to the power supply through chassis or System Ground 170, 270. This 'other path' presents an additional load to the high voltage power supply; thus, the delivered current increases. The return current through the return electrode remains the same since the new load created by a fault in the system is in parallel with the return circuit. Therefore, if the difference between the delivered and return current is greater than a set parameter in a system control of CE analysis system 130, an error is flagged in some embodiments.

However, in a CE ESI-MS configuration, such as the one shown in FIG. 1A, the mass spectrometer provides another path for CE current to flow through MS HV supply 104. While the conductive fluid capillary 144 provides a path to ground for the separation current, in some embodiments the MS HV power supply 104 is of much lower resistance, so a majority of return separation current flows through MS ESI HV power supply 104 and returns through a chassis ground of the CE analysis system 130. The CE current thus bypasses any potential return current detection circuit that is inside the CE power supply. If the return CE current is measured on the high side of the MS ESI power supply, though, this current is thereby measured prior to any return through the chassis ground.

In many embodiments, fixed systems for CE, ESI-MS, or both are used, such that the internal structure cannot be altered to include such a current sense circuit in the correct position. In such alternative embodiments, the current sense circuit is a separate device, or is integrated into a CE or ESI-MS system. In one potential embodiment, to avoid changing the mass spectrometer, the current sense circuit is on the high side (output) of the MS high voltage power supply to connect via a MS HV supply terminal, as shown in FIG. 1A.

FIG. 1C illustrates one potential embodiment of a current sensing circuit according to one potential implementation of the innovations presented herein. FIG. 1C includes limit resistor 184, sense resistor 182, amplifier 192, DC/DC converter 190, amplifier 194, and voltage protection device 186.

A DC/DC converter 190 functions for providing voltage outputs for amplifier 192 while allowing amplifier 192 to be isolated and to float on the high voltage output of MS ESI HV power supply 104. In certain embodiments, a voltage protection device is coupled from the DC/DC converter floating ground terminal 172 to a system ground 270 to prevent damage in certain circumstances. In alternative embodiments, DC/DC converter 190 is rated for a large voltage, such that it can withstand having the entire voltage load from MS HV power supply 104 and the CE HV power supply (102) placed across a DC/DC ground terminal 197 to the DC/DC converter floating ground terminal 172.

In embodiments with a floating sense circuit, position of the current sense resistor 182 on the high side of the MS HV supply 104 requires some form of an isolation or connection from the floating node to the system ground. In some embodiments, DC/DC converter 190 provides power to and isolates the current sense circuit in embodiments with a floating node. In certain fault or error configurations where the sprayer tip for electrospray at the MS input is not near a surface to which it can spray, and the power cable is unplugged from the MS power supply, the full magnitude of the CE supply can appear across the DC/DC converter 190. For this reason, a voltage protection device 186 is included in certain embodiments. In one potential embodiment, voltage protection device 186 comprises gas discharge tubes. In a further embodiment, gas discharge tubes are configured to clamp the voltage across the converter to a value less than the rating of the DC/DC converter which may be, for example 10 kV with a tolerance of +/−20%. In alternative embodiments, devices with other ratings and tolerances may be use.

In the event there is leakage at the electrospray junction or return electrode, limit resistor 184 protects the sense circuit from the MS ESI HV power supply because it forms a resistive divider with the sense resistor 182 and any further resistor in the cable from the MS supply. As a non-limiting example, in one potential embodiment, limit resistor 184 is a 10 megaOhm resistor. In some embodiments limit resistor 184 with MS supply cable resistance limits the current in case the user unplugs the connection from the CE analysis system 130 while the MS HV supply 104 is on. In one potential embodiment with a maximum MS HV voltage setting of 10 kV, the limit resistor 184 with a 10 megaOhm resistance limits the current to 1 mA. This is in addition to any current limiting that is designed into the mass spectrometer.

In some embodiments, in addition to dealing with the fault or error conditions discussed above, the current sense signal must be communicated across the isolation level, essentially creating a current sense signal path from the floating sense resistor to a controller that executes a fault or error based on the signal. In other embodiments, the current sense signal path includes elements such as amplifier 192, amplifer 194, DC/DC converter 190, and any other such elements. In certain embodiments, DC/DC converter 190 includes a built in isolated analog channel which is used to transmit the current sense signal from floating amplifier 192 across the isolation via DC/DC converter 190 to amplifier 194 on the system ground side. In some embodiments such an analog channel comprises separate 'analog up' and 'analog down' channels for transmitting signals to and from the isolated and grounded sides of the circuit. In one potential embodiment, such up and down channels accommodate 0-10V signals with a gain error of +/−2% and linearity error of +/−0.05% on signals from DC to 4 Hz. In other embodiments, alternative paths such as wireless or fiber optic channels are used to communicate the sense signal.

Voltage limit resistor 184 acts as a current limit resistor which protects both the current sense circuit 143 (that includes amplifier 192) and also the MS HV power supply 104 in the event of a failure. One non-limiting example of such a failure that is detectable by sense resistor 182 and amplifier 192 is the formation of a salt bridge during capillary electrophoresis operation.

In some embodiments, along with voltage limit resistor 184, sense resistor 182 and amplifier 192 are part of a current sense circuit that detects leakage current. Whereas in standard CE ESI-MS systems, a visual or data based failure of sample separation or some other obvious system failure in the data may be the first sign of system failure, the use of a current sense circuit provides feedback to automatically shut down operation if a fault mode is detected. The salt bridge failure mentioned above is a non-limiting example of a failure which is detectable using some embodiments of the current sense circuit.

If leakage occurs, the voltage across the voltage limit resistor 184, which has a high value, prevents damage to the amplifier 192 and the (non-isolated, non-floating) mass spectrometer ESI HV power supply 104 connected to current sense input terminal 178 because most of the voltage will appear across this voltage limit resistor 184. One non-limiting potential example of a high value voltage limit resistor 184 is a resistor having a value of 200 megaOhms. The DC/DC converter 190 is functionally in parallel with the current sense resistor 182, the voltage limit resistor 184, and the (non-isolated, non-floating) MS HV power supply 104. In certain embodiments, the DC/DC power converter 190 is designed to withstand the sum of the CE separation capillary and electrospray voltages in order to avoid damage to the system.

In certain embodiments, the separation current is on the order of 1 uA in GE-MS mode. In such embodiments, the return current signal may be 0-10V, which is interpreted as 0-30 uA. With a 10V ceiling, a 33.2 kOhm sense resistor 182 gives a resolution of 30.1 uA per volt.

As described above for power supply ratings, the resistor values of voltage limit resistor 184 and sense resistor 182 are not limited to the specific values used for example purposes. For example, a current sense resistor according to some embodiments of the present innovations includes any value that enables the current sensing function and allows the described system to function. A current sense resistor, in one embodiment, comprises a resistor having a rating value from 7 kOhms to 503 kOhms.

In various alternative embodiments, voltage limit resistor 184 may be selected to have a resistance in the range of 1-200 megaOhms. In various alternative embodiments, the resistance may be in range of 1-100 megaOhms, in a range of 1-50 megaOhms, or in a range of 1-20 megaOhms. Such a limit resistory may be selected to optimize power usage and sensitivity of the voltage limit resistor, and may be matched to complement other selected values in a particular system.

In additional various alternative embodiments, sense resistor 182 may be selected to have a resistance in the range of 1-300 kOhm. In various alternative embodiments, the resistance may be in a preferred range of 1-100 kOhms, in a more preferred range of 1-50 kOhms, or in an even more preferred range of 1-40 kOhms. The various embodiments may be implemented to select particular sensitivities for sensing in a current sense circuit, with the current and/or voltage values in the senseing circuit adjusted by the selection of the sense resistor.

In various alternative embodiments, an in-cable resistor that is part of CE ESI-MS system 100 may be selected to have a resistance in the range of 1-100 megaOhm. In various alternative embodiments, the resistance may be in a preferred range of 1-50 megaOhms, or in a more preferred range of 1-20 megaOhms.

In additional various alternative embodiments, voltage protection device 186 may be selected to have a leakage current rating of less than 100 pA with a high voltage protection rating of 10-14 kV. In various alternative embodiments, the rating may be in a preferred range of 10-12 kV.

In additional various alternative embodiments, MS HV Power supply 104 may provide a voltage of 0-10 kV. In additional various alternative embodiments, CE HV Power supply 102 may provide a voltage of 0-60 kV In various alternative embodiments, the rating may be in a range of 0-40 kV, in a range of 0-35 kV, or in a range of 0-30 kV.

Further, in various other alternative embodiments, any value may be selected that enables the system to operate in accordance with the innovations presented herein, and the various embodiments described above may be selected to optimize for particular voltage values across both the CE high voltage supply and the MS high voltage supply with an optimized current sensing circuit set to the particular system to implement trade-offs in a fault detection circuit between sensitivity, reliability, and power usage. A first embodiment may thus use more power and have a higher error rate in exchange for higher sensitivity, while other embodiments may prioritize other characteristics of a system with fault detection as described herein.

Additionally, alternative embodiments use alternative forms of current sense circuits. Additional examples of current sense circuits include Hall Effect Sensors and Rogowski Coil Sensors.

In some embodiments wherein the CE power supply is bipolar so that the CE current can flow in both directions through sense resistor 182, amplifier 192 is an absolute value amplifier to accommodate bipolar operation. In alternative embodiments, amplifier 192 comprises multiple amplifiers or buffers in combination, such as, as a non-limiting example, a buffer amplifier followed by an absolute value amplifier.

Amplifier 194 is included in some, but not all, embodiments of the innovations. Amplifier 194 is a buffer amplifier to assist in outputting the sense signal from sense resistor 182 to a control system. The control system is selected from the group consisting of a CE controller 110, an MS controller 160, a control function such as an embedded microcontroller, or a combination thereof.

Additional alternative embodiments use analog to digital converters, digital to analog converters, or fiber optic or other signal paths for the sense signal. In one potential alternative embodiment, voltage to frequency and frequency to voltage converters are used to convert the signal to and from a digital stream and fiber optics are used to transmit the current sense signals from an isolated side of the system to a grounded side of the current sense circuit, and then out to a control system.

Figure 4:
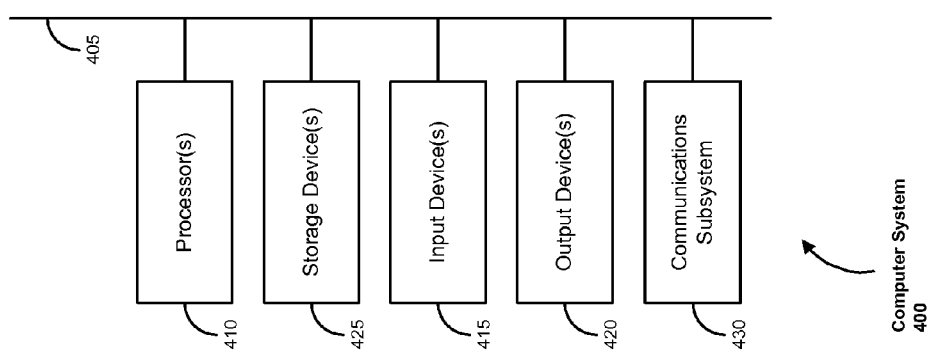
FIG. 4 illustrates one potential embodiment of a computer system or controller that is used in conjunction with a CE-ESI mass spectrometry system in accordance with various embodiments of the innovations presented herein.

In some embodiments, CE controller 110, MS controller 160, or both are stand-alone computing devices or any other acceptable device, as further described by FIG. 4. In some further embodiments controllers function to manage the operation of any component in the system, to receive and analyze data from any part of the system, and to monitor components of the system for errors. In particular, in some embodiments one or more controllers are configured to receive a current sense signal from a current sense output such as current sense sensor output 198 that is used to identify a fault in the system. Additionally, in various embodiments, CE controller 110 and MS controller 160 are integrated with their respective analysis systems so that CE controller 110 is integrated with CE Analysis System 130, MS controller is integrated with mass spectrometer 150, or both. Additionally, in certain embodiments, any of the above described components are integrated with any other component.

Certain embodiments include additional elements to compensate for offsets and errors. Some of these embodiments implement offsets via calculations in controllers such as CE controller 110 or MS controller 160, or alternatively implement offsets in hardware or using embedded systems. As a non-limiting example, in one potential embodiment, a 10-16 mV offset in the analog channel of the DC/DC converter causes an offset of 0.3 to 0.48 uA. In some embodiments, such errors are minimized or compensated for in controller calculations or other reading and error reporting adjustments.

Further, in some embodiments, connecting a MS ESI HV voltage supply 104 to a capillary junction at MS inlet 153 causes a current to flow through the conductive fluid capillary. In some further embodiments, a return current signal has its own dedicated input to a system board, so the current through the conductive fluid capillary is measured separately from the other elements and currents of the system. Since the vast majority of this conductive fluid current is induced by the MS high voltage power supply 104, it also passes through the current sense circuit 143. In some embodiments of the innovations, this current is therefore measured in the system board and the value of this induced current is deducted from the value of the current of the current sense circuit to provide correct leakage current readings. In alternative embodiments, this induced current is eliminated by removing the return electrode from the system and compensating for the alternative electrical structure.

In addition, in some embodiments control systems are implemented to automatically flag errors. For example, in one embodiment, CE controller 110 is coupled to current sense sensor output 198 to receive a current sense signal. Noise or other various errors may cause individual readings from current sense sensor output 198 to be innacurate due to expected spikes in the current through sense resistor 182. In one potential embodiment, CE controller 110 records a reading over a threshold and flags the reading without creating an error message. In certain embodiments, whenever a reading is over the threshold, an additional flag is set, and whenever a reading is within the acceptable threshold, a flag is removed to a minimum of zero flags. In some embodiments, when the system reaches a certain number of flags to reach an error flag number, an error message is created or an automatic shutdown is implemented. Thus, such systems avoid unnecessary false errors or shutdowns caused by noise through sense resistor 182 or anywhere else in the system while maintaining system protections. In one potential embodiment, a 0.4 microamp offset is integrated into the system to accommodate hardware inaccuracy. In further potential embodiments, the delivered current, minus the return, sense, and offset currents, is given a threshold of three microamps, with readings above this threshold creating flags and readings below this threshold removing flags.

Additionally, various embodiments use a floating control that is isolated from chassis ground but maintains a link to CE analysis system across an electrically isolated communication link. In various embodiments, the communication link comprises a wireless communication link. Alternatively, in some embodiments, the communication link comprises an optical communication link such as a link via an optical fiber. An optical fiber communication link provides the benefit of being highly resistive and therefore able to function across the isolation when an isolated embodiment of HV CE power supply is floating on a large voltage. In some embodiments, optical coupler devices, with a sufficient isolation rating, are used directly to pass digital inputs and outputs. Because power supply units, such as a CE power supply, frequently require analog input controls but optical couples are not directly functional for most such controls, in some embodiments of the innovations, analog signals are first converted to a digital pulse stream, routed through the same optical coupler devices used for any digital signals, and then reconstructed back into analog signals.

Figure 2:
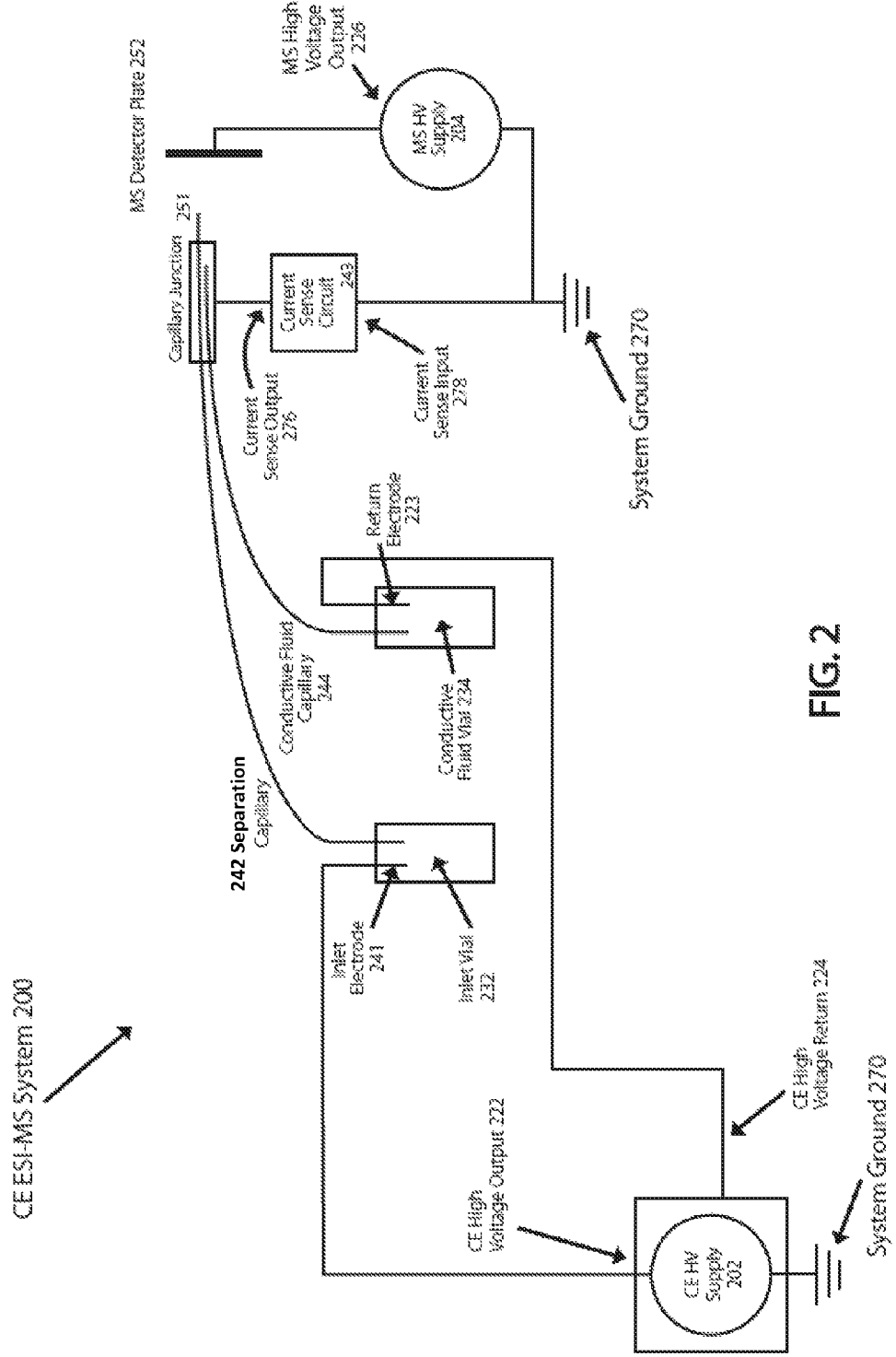
FIG. 2 illustrates an electrical diagram of one potential implementation of a CE-ESI mass spectrometry system in accordance with one potential embodiment of the innovations presented herein.

FIG. 2 shows an alternative configuration of a CE ESI-MS system according to another alternative embodiment of the present innovations. FIG. 2 shows a system where the high voltage output of the MS HV power supply 204 is applied to the MS Detector Plate 252. In such grounded CE ESI-MS systems 200, as well as in embodiments without a current detecting circuit, the leakage current may be extremely difficult to detect or may only be detectible with high margins of error because the leakage current returns to the CE high voltage power supply along with the current delivered to the CE separation capillary by bypassing the return current terminal in the CE high voltage supply. The current delivered to the CE 'separation capillary' will not return to the CE high voltage power supply through its return terminal (shown as CE HV return); instead it returns through the System Ground 270. The leakage current will bypass all of the other circuitry, capillaries, and power supplies and return to the CE high voltage power supply through the connection to ground. To sense the current flowing through the separation capillary 242, the current sense resistor which in some embodiments has a value in the order of 500 kOhms, is inserted between the Capillary Junction 251 and the System Ground 270. The separation capillary 242, also called a sample capillary, is in some embodiments a high-sensitivity porous sprayer capillary (HSPS capillary) that is useful for sheathless ESI.

The voltage across the current sense resistor then represents the sum of the electrospray ionization current delivered by the (non-isolated, non-floating) MS HV power supply 204 and the current through the separation capillary 242 delivered by the CE HV Power Supply 202. An amplifier measures this voltage, and an absolute value amplifier ensures the signal can be read if the power supply polarity is reversed.

In contrast to the floating embodiment of FIG. 1, because the sense resistor or any other circuit is coupled to ground, the isolation elements, such as a DC/DC converter, are not required to provide isolation in some embodiments of the innovations. In certain embodiments, a CE analysis system and current sense circuit include elements to deal with isolation as described above, and in further embodiments additionally function in a configuration for non-isolated embodiments such as the one shown in FIG. 2.

Thus, in certain embodiments, CE analysis system 130 and current sense circuit 143 are initially coupled to a first mass spectrometer 150 having the Current Sense Circuit 143 floating on the MS HV supply 104 as shown in FIG. 1A-1B. The system may then be reconfigured to have CE analysis system 130 and current sense circuit 243 coupled to a second mass spectrometer having a second MS HV supply 204 with current sense circuit 243 coupled to MS HV supply 204 in a non-floating configuration. The system may thus allow integration of a single CE system, such as Beckman PA 800 plus capillary electrophoresis system, with different types of MS systems, such as Bruker-type mass spectrometers in a non-floating current sense configuration and non-Bruker type mass spectrometers in a floating current sense configuration. Non-limiting examples of a non-Bruker type mass spectrometer include a Thermo MS, an AB-Sciex MS, or a Waters MS.

In certain embodiments, the high voltages from CE HV supply 102 and MS HV supply 104 create significant amounts of heat. In various alternative embodiments, coolant tubes are placed around both separation capillary 142 and conductive fluid capillary 144 for heat dissipation. In certain such embodiments the tubes carry a coolant to the sprayer housing with the capillaries threaded through the coolant tubes such that the tubes, and the coolant carried by the tubes, surround the capillaries.

Figure 3:
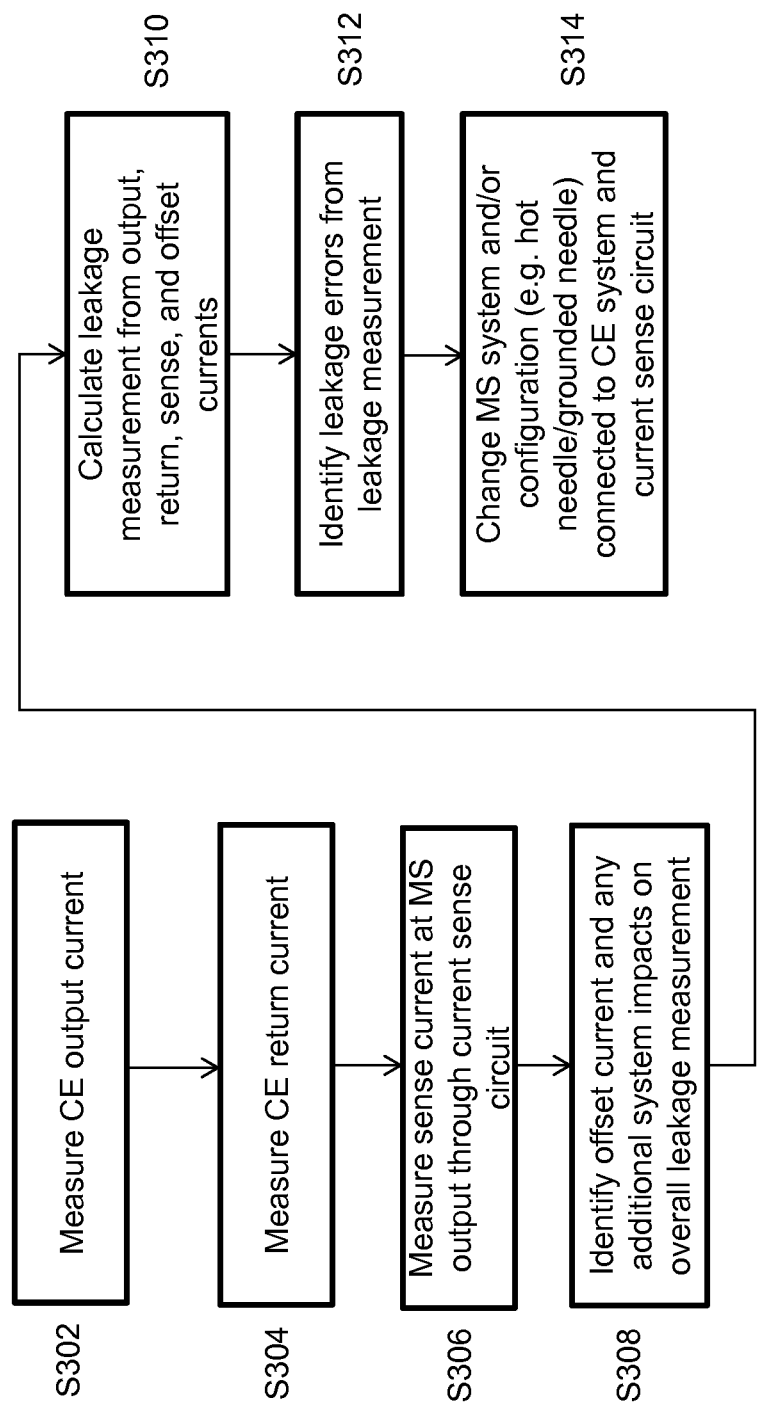
FIG. 3 illustrates a method of using a CE analysis system including improved error detection in accordance with one potential implementation of a CE-ESI mass spectrometry system consistent with the innovations presented herein.

FIG. 3 illustrates one potential method of using an improved CE system with error detection in accordance with the present innovations. In S302, output at a CE HV supply such as CE HV supply 102 is measured. In S304, return current at CE high voltage return input 124 is measured. In S306, sense current from current sense circuit 143 is measured. In some embodiments this measurement is from a current sense signal path from sense resistor 182 to amplifier 192 to DC/DC converter 190 to amplifier 194 to current sense sensor output 198 to CE controller 110, or by any other method in various alternative embodiments.

In S308, any offset or error associated with system hardware or software inaccuracy is identified. In some embodiments, this simply is a recorded value stored in CE controller 110 or is a measured value. In certain embodiments, this offset includes an offset due to an induced return current signal caused by connecting the MS high voltage power supply to the capillary junction as described above.

In S310, a leakage current is calculated by subtracting return, sense, and offset currents from the output delivered current of the CE high voltage power supply output 122. CE controller 110 then implements various methods to identify errors from the calculated leakage current. Finally, in S314, the system is reconfigured while maintaining the benefit of the improved current or leakage detection merely by connecting a new mass spectrometer in place of the previous mass spectrometer. This enables the CE system to individually interface with multiple mass spectrometers having different structures, inputs, and system values, while maintaining the improved error detection functionality associated with the current sense circuit.

In various embodiments, offset values are automatically adjusted or compensated for as part of step S316 when a new MS system is connected. Further, in some embodiments, any system described herein is integrated with additional interface functions such as electrospray adapter modules and software configurations to enable a CE system to connect to different mass spectrometer systems through connections at a MS inlet 153 and MS power supply terminal.

FIG. 4 provides a schematic illustration of one embodiment of a computer system 400 that in some embodiments is used with aspects of an improved CE-ESI-MS system, as described herein, and/or functions, for example, as various parts of capillary electrophoresis controller 110, mass spectrometer controller 160, CE analysis system 130, power supply 102, or mass spectrometer 150 of FIG. 1. In some embodiments, computer system 400 is considered to be usable in a potential embodiment for any component that requires control or electronic communication. It should be noted that FIG. 4 is meant only to provide a generalized illustration of various components, any or all of which may be utilized, as appropriate. FIG. 4, therefore, broadly illustrates how individual system elements are implemented in various embodiments in a relatively separated or relatively more integrated manner.

The computer system 400 is shown comprising hardware elements that in certain embodiments are electrically coupled via a bus 405 (or may otherwise be in communication, as appropriate). In some embodiments, the hardware elements include one or more processors 410, including, without limitation, one or more general-purpose processors and/or one or more special-purpose processors (such as digital signal processing chips, graphics acceleration chips, and/or the like); one or more input devices 415, which in some embodiments include, without limitation, a mouse, a keyboard, and/or the like; and one or more output devices 420, which in some embodiments include, without limitation, a display device, a printer, and/or the like.

In some embodiments the computer system 400 further includes (and/or is in communication with) one or more storage devices 425, which in certain embodiments comprise, without limitation, local and/or network accessible storage and/or include in some embodiments without limitation, a disk drive, a drive array, an optical storage device, a solid-state storage device such as a random access memory ("RAM") and/or a read-only memory ("ROM"), which in some further embodiments are programmable, flash-updateable, and/or the like. In some embodiments the computer system 400 also includes a communications subsystem 430, which in further embodiments includes, without limitation, a modem, a network card (wireless or wired), an infra-red communication device, a wireless communication device, and/or chipset (such as a Bluetooth® device, an 802.11 device, a WiFi device, a WiMax device, cellular communication facilities, etc.), and/or the like. In certain embodiments the communications subsystem 430 permits data to be exchanged with a network (such as the network described below, to name one non-limiting example), and/or any other devices described herein. In many embodiments, the computer system 400 will further comprise a working memory or additional memory systems, which in some embodiments include a RAM or ROM device, as described above.

The computer system 400 also comprises, in some embodiments, software elements which comprise computer programs of the invention, and/or are designed to implement methods of the invention and/or configure systems of the invention, as described herein. Merely by way of non-limiting example, in certain embodiments one or more procedures described with respect to the method(s) discussed above are implemented as code and/or instructions executable by a computer (and/or a processor within a computer). In some embodiments, a set of these instructions and/or code is stored on a non-transitory computer readable storage medium, such as the storage device(s) described above. In some embodiments, the storage medium is incorporated within a computer system. In other embodiments, the storage medium is separate from a computer system (i.e., a removable medium, such as a compact disc, etc.), and/or is provided in an installation package, such that the storage medium is used to program a general purpose computer with the instructions/code stored thereon. In some embodiments, these instructions take the form of executable code, which is executable by the computer system and/or takes the form of source and/or installable code, which, upon compilation and/or installation on the computer system (e.g., using any of a variety of generally available compilers, installation programs, compression/decompression utilities, etc.), then takes the form of executable code.

It will be apparent to those skilled in the art that substantial variations may be made in accordance with specific requirements. For example, in some embodiments customized hardware also is used, and/or particular elements are implemented in hardware, software (including portable software, such as applets, etc.), or both. In further embodiments, connection to other computing devices such as network input/output devices is employed.

The terms "machine-readable medium" and "computer readable medium", as used herein, refer to any medium that participates in providing data that causes a machine to operate in a specific fashion. In some embodiments implemented using the computer system 400, various machine-readable media are involved in providing instructions/code to processor(s) 410 for execution and/or are used to store and/or carry such instructions/code (e.g., as signals). In many implementations, a computer readable medium is a physical and/or tangible storage medium. Such a medium may take many forms, including but not limited to, non-volatile media, volatile media, and transmission media. Non-volatile media includes, as a non-limiting example, optical or magnetic disks, such as the storage device(s) 425. Volatile media includes, without limitation, dynamic memory, such as the working memory. Transmission media includes coaxial cables, copper wire, and fiber optics, antenna, including the wires that comprise the bus 405, as well as the various components of the communications subsystem 430 (and/or the media by which the communications subsystem 430 provides communication with other devices). Hence, in some embodiments transmission media also takes the form of waves (including, without limitation, radio, acoustic, and/or light waves, such as those generated during radio-wave and infra-red data communications).

In certain embodiments various forms of machine-readable media are involved in carrying one or more sequences of one or more instructions to the processor(s) 410 for execution. Merely by way of non-limiting example, the instructions in some embodiments are initially carried on a magnetic disk and/or optical disc of a remote computer. In some embodiments, a remote computer loads the instructions into its dynamic memory and sends the instructions as signals over a transmission medium to be received and/or executed by the computer system 400. These signals, which in some embodiments are in the form of electromagnetic signals, acoustic signals, optical signals, and/or the like, are all examples of carrier waves on which instructions are encoded, in accordance with various embodiments of the invention.

The communications subsystem 430 (and/or components thereof) generally will receive the signals, and the bus 405 in some embodiments then carries the signals (and/or the data, instructions, etc., carried by the signals the processor(s) 405 which executes the instructions.

Capillary electrophoresis as described herein is an intrinsically low flow separation technique and includes, but is not limited to, Capillary Zone Electrophoresis (CZE; also known as free-solution CE [FSCE]), Capillary Gel Electrophoresis (CGE), Capillary Isoelectric Focusing (CIEF), Isotachophoresis (ITP), Electrokinetic Chromatography (EKC), MicellarElectrokinetic Capillary Chromatography (MECC OR MEKC), Micro Emulsion Electrokinetic Chromatography (MEEKC), Non-Aqueous Capillary Electrophoresis (NAGE), and Capillary Electrochromatography (CEC).

Uses of the innovations herein include, but are not limited to, characterizing therapeutic proteins; identifying proteins that make up a specific proteome; characterizing post-translational modifications; studying a metabolomic fingerprint related to a particular condition; and quantifying drugs and their metabolites in a minute or complex sample matrix.

While the invention has been described with respect to exemplary embodiments, one skilled in the art will recognize that numerous modifications are possible. For example, the methods and processes described herein may be implemented using hardware components, software components, and/or any combination thereof. Further, while various methods and processes described herein are described with respect to particular structural and/or functional components for ease of description, methods of the invention are not limited to any particular structural and/or functional architecture but instead are in some embodiments implemented on any suitable configuration. Similarly, while various functionalities are ascribed to certain system components, unless the context dictates otherwise, in some embodiments this functionality is distributed among various other system components in accordance with different embodiments of the invention.

As described above, potential uses include analysis of protein complexes, proteins, peptides, glycans or drugs/metabolites using CE; and characterize/identify the separated molecules using MS. Additionally, the innovations herein in some embodiments are used with molecular analysis, protein analysis, carbohydrate analysis, glycoprotein analysis, small molecule analysis, chiral analysis, ion analysis, drug analysis, and genetic analysis. DNA sequencing, genotyping, single nucleotide polymorphism (SNP) analysis, short tandem repeat (STR) analysis, DNA fingerprinting analysis, nucleic acid analysis, genotyping analysis, oligonucleotide purity analysis, plasmid analysis, single-stranded conformational polymorphism (SSCP) analysis, and quantification by direct hybridization analysis. Further, this list is not exhaustive and is not limiting, as a person of ordinary skill in the art may recognize additional potential uses for various embodiments according to the innovations described herein.

Moreover, while the procedures comprised in the methods and processes described herein are described in a particular order for ease of description, unless the context dictates otherwise, various procedures may be reordered, added, and/or omitted in accordance with various embodiments of the innovations. Moreover, the procedures described with respect to one method or process in some embodiments are incorporated within other described methods or processes; likewise, system components described according to a particular structural architecture and/or with respect to one system in some embodiments are organized in alternative structural architectures and/or incorporated within other described systems. Hence, while various embodiments are described with—or without—certain features for ease of description and to illustrate exemplary features, the various components and/or features described herein with respect to a particular embodiment are in certain embodiments substituted, added, and/or subtracted from among other described embodiments, unless the context dictates otherwise. Consequently, although the invention has been described with respect to exemplary embodiments, it will be appreciated that the invention is intended to cover all modifications and equivalents within the scope of the following claims.

What is claimed is:

1. A capillary electrophoresis system for use in conjunction with electrospray ionization mass spectrometry systems comprising:
   a capillary electrophoresis (CE) high voltage power supply having an output and an input;
   a CE output current detector at the output of the CE high voltage power supply to detect a delivered current;
   a CE return current detector at the input of the CE high voltage power supply to detect a return current;
   a mass spectrometry (MS) power supply that connects to a high voltage input of a current sense circuit,
   wherein the CE high voltage power supply and the MS power supply are electrically coupled to a system ground;
   a current sense circuit coupled to a MS power supply terminal, such that the MS power supply terminal provides a potential that is electrically coupled to the input of the CE high voltage power supply via the current sense circuit, a conductive fluid capillary, and a return electrode, and wherein the potential provided by the MS power supply terminal is further electrically coupled to the output of the CE high voltage power supply via the current sense circuit, a separation capillary, and an inlet electrode; and
   a comparison circuit that compares the delivered current, the return current, and a current sensed by the current sense circuit to detect a leakage current.

2. The system of claim 1 wherein the current sense circuit comprises a sense resistor and buffer amplifier coupled to an absolute value amplifier.

3. The system of claim 2 wherein the current sense circuit further comprises a DC/DC converter coupled to the absolute value amplifier and powering the buffer and absolute value amplifiers;
   wherein an isolated side of the current sense circuit is floating.

4. The system of claim 3 further comprising a voltage protection device coupled from a system ground to a floating ground of the current sense circuit.

5. The system of claim 4 wherein the voltage protection device comprises a gas discharge tube.

6. The system of claim 2 further comprising a current sense signal path from the sense resistor to a controller.

7. The system of claim 6 wherein the controller is a microprocessor of a CE analysis system.

8. The system of claim 6 wherein the current sense signal path comprises the sense resistor coupled to the buffer amplifier, the absolute value amplifier, an isolated communication path, and a current sense output.

9. The system of claim 8 wherein the isolated communication path is an analog channel through a DC/DC converter that transmits analog signals to and from an isolated and a grounded side of the DC/DC converter.

10. The system of claim 8 wherein the isolated communication path comprises a wireless signal.

11. The system of claim 8 further comprising a conductive fluid current sensor coupled to the current sense circuit via a capillary junction and to the return electrode, wherein a conductive fluid current signal is offset from a current sense signal to create a leakage signal.

12. The system of claim 11 wherein the CE input current detector creates a return current signal.

13. The system of claim 12 wherein the CE output current detector creates a delivered current signal.

14. The system of claim 13 wherein the controller comprises an offset current signal that is associated with a system inaccuracy.

15. The system of claim 14 wherein the controller calculates a leakage current by subtracting the return current signal, the current sense signal, and the offset current signal from the delivered current signal.

16. The system of claim 15 wherein the controller creates an error signal if the leakage current exceeds a predetermined threshold.

17. The system of claim 16 wherein the controller initiates an automatic system shutdown when a number of leakage current readings above the predetermined threshold exceeds a number of leakage current readings below the predetermined threshold for a number of readings by an error flag number.

18. The system of claim 13 wherein the current sense circuit comprises a Hall Effect Sensor, a Rogowski Coil Sensor, or a combination thereof.

19. The system of claim 1 wherein a current sense input terminal is directly coupled to the system ground.

20. The system of claim 1 wherein the current sense circuit further comprises a limit resistor coupled from a sense resistor to an electrospray terminal or capillary junction.

21. The system of claim 20 wherein the limit resistor comprises a value selected from a group consisting of a resistor value of from 1 megaOhm to 200 megaOhms (inclusive), of from 1 megaOhm to 100 megaOhms (inclusive), of from 1 megaOhm to 50 megaOhms (inclusive), and from 1 megaOhm to 20 megaOhms (inclusive).

22. A capillary electrophoresis electrospray ionization mass spectrometry (CE-ESI-MS) system comprising:
   a mass spectrometry (MS) high voltage power supply having a first output, a first return and a first ground;
   a capillary electrophoresis (CE) high voltage power supply having a second output, a second return and a second ground, said second ground including a connection to the first ground;
   a CE output current detector at the output of the CE high voltage power supply to detect a delivered current;

a CE return current detector at the input of the CE high voltage power supply to detect a return current;

a MS electrical path that provides the MS high voltage power supply first return from the first output to the first ground via a MS load;

a CE electrical path that provides the CE high voltage power supply second return from the second output to the second ground via a separation capillary, wherein a resistive electrical path of the separation capillary is connected to the first output and wherein the first output is electrically coupled to the second return via the separation capillary;

a current sense circuit coupled to the first output and to the separation capillary via a capillary junction; and a comparison circuit that compares the delivered current, the return current, and a current sensed by the current sense circuit to detect a leakage current.

23. A method of operating a capillary electrophoresis electrospray ionization mass spectrometry system comprising:

measuring a sense current from an electrospray capillary junction to a mass spectrometry (MS) DC high voltage power supply at a MS supply terminal of the MS DC high voltage power supply;

measuring a delivered current at a capillary electrophoresis (CE) output of a CE high voltage power supply;

measuring a return current at a CE return of the CE high voltage power supply, wherein the CE return and the CE output are electrically coupled to the electrospray capillary junction, and the MS DC high voltage power supply and CE high voltage power supply are coupled to a ground;

comparing the sense current, the delivered current, and the return current to calculate a leakage current; and creating a fault error when the calculated leakage current exceeds a threshold.

24. A method comprising measuring a delivered current at an output of a capillary electrophoresis (CE) power supply;

measuring a return current at a return of the CE power supply;

identifying an offset current associated with system inaccuracy;

measuring a sense current at a current sense circuit at a terminal of a mass spectrometry (MS) high voltage power supply, wherein the terminal of the MS high voltage power supply, the return of the CE power supply, and the output of the CE power supply are electrically coupled to an electrospray capillary junction, and wherein the MS high voltage power supply and CE power supply are coupled to a ground; and identifying a leakage current by subtracting the return current, the sense current, and the offset current from the delivered current.

* * * * *